United States Patent
Ohira et al.

[19]

[11] Patent Number: 5,945,004
[45] Date of Patent: Aug. 31, 1999

[54] METHOD AND APPARATUS FOR TREATING WASTE LIQUIDS CONTAINING BODY FLUIDS

[75] Inventors: Junichi Ohira; Junichi Yamanaka; Satoru Toyoshima; Koichi Murayama, all of Sakai, Japan

[73] Assignee: Daiken Iki Co., Ltd., Osaka, Japan

[21] Appl. No.: 08/930,248

[22] PCT Filed: Jan. 29, 1997

[86] PCT No.: PCT/JP97/00251

§ 371 Date: Oct. 1, 1997

§ 102(e) Date: Oct. 1, 1997

[87] PCT Pub. No.: WO97/27883

PCT Pub. Date: Jul. 8, 1997

[30] Foreign Application Priority Data

Feb. 1, 1996  [JP]  Japan .................................. 8-016859

[51] Int. Cl.⁶ .................................................. C02F 1/56
[52] U.S. Cl. .......................... 210/710; 210/721; 210/728; 210/730; 210/732; 210/737; 210/738; 210/764; 210/769; 210/202; 210/206; 210/208; 210/257.1; 210/258; 422/1; 422/28; 588/258; 604/317; 604/403; 604/408; 604/416
[58] Field of Search ..................... 210/710, 721, 210/737, 764, 769, 181, 202, 206–208, 257.1, 728, 730, 732, 258; 422/1, 28; 588/258; 604/317, 403, 406, 416, 408

[56] References Cited

U.S. PATENT DOCUMENTS

| 5,238,582 | 8/1993 | Hori et al. ........................ 210/749 |
| 5,254,285 | 10/1993 | Fujita .............................. 252/175 |
| 5,437,836 | 8/1995 | Yamada ........................... 422/1 |
| 5,549,585 | 8/1996 | Maher et al. .................... 604/317 |
| 5,549,820 | 8/1996 | Bober et al. .................... 210/199 |
| 5,741,237 | 4/1998 | Walker ........................... 604/317 |
| 5,741,238 | 4/1998 | Bradbury et al. ............... 604/322 |
| 5,776,118 | 7/1998 | Seifert et al. .................. 604/317 |

FOREIGN PATENT DOCUMENTS

| 51-48589 | 10/1974 | Japan . |
| 4-60713 | 9/1992 | Japan . |
| 5-31163 | 2/1993 | Japan . |
| 5-293166 | 11/1993 | Japan . |
| 6-36813 | 5/1994 | Japan . |
| 1-96558 | 4/1998 | Japan . |

*Primary Examiner*—Peter A. Hruskoci
*Attorney, Agent, or Firm*—Oblon, Spivak, McClelland, Maier & Neustadt, P.C.

[57] ABSTRACT

A method and apparatus for treating waste liquids containing body fluids so as to prevent problems such as nosocomial infection due to such waste liquids containing body fluids discharged from patients under (surgical) operation or treatment, particularly those waste liquids containing blood or an irrigation liquid used to irrigate the body cavity of such patient. The method includes collecting a waste liquid containing body fluids into a container, separating the waste liquid into a supernatant liquor and a flocculate within the container, discharging the supernatant liquor from the container, and disposing of the flocculate remaining in the container together with the container.

11 Claims, 8 Drawing Sheets

METHOD AND APPARATUS FOR TREATING WASTE LIQUIDS CONTAINING BODY FLUIDS

This is a 371 of PCT/JP97/00251, filed Jan. 29, 1997.

BACKGROUND OF THE INVENTION

1. Field of the Invention

The present invention relates to method and apparatus for treating waste liquids containing body fluids so as to prevent problems such as nosocomial infection due to such waste liquids containing body fluids discharged from patients under (surgical) operation or treatment, particularly those waste liquids containing blood or irrigation liquid used to irrigate the body cavity of such patient.

2. Discussion of the Background

Nosocomial infection currently at issue in Japan has rapidly become a serious problem with the medical progress in the last dozen of years. Infection to compromised patients and occupational infection to persons engaged in medical treatments are particularly problematic.

Although the nosocomial infection occurs in various ways, secondary infection from a waste liquid containing body fluids, particularly blood, an irrigation liquid (isotonic sodium chloride solution) used to irrigate the body cavity, or a like fluid, discharged from a patient under surgical operation or treatment (hereinafter termed "waste liquid" for simplicity) to surroundings including personnel engaged in medical treatments and other patients is a serious problem. In 1989 the Japanese Welfare Ministry issued "Guideline for disposal of medical wastes" as a measure to prevent the nosocomial infection. According to the Guideline, all bloods and blood-adhering matters should be regarded as infectious industrial waste and should be subjected to incineration disposal or entrusted to professionals of waste disposal after they have been sterilized or disinfected.

The waste liquid usually contains a body cavity irrigation liquid in a considerable amount. This imposes a great expense on hospitals for treating the waste liquid.

Various proposals have been made to overcome this situation.

Collecting bottles, for example, have conventionally been used as waste liquid treating containers. Such collecting bottles generally are relatively heavy and easy to break and, hence, dangerous to persons handling the bottles. In addition, there are required time and labor for disinfecting or sterilizing an infectious waste liquid before its disposal and for washing used bottles later. In view of this, containers of synthetic resin have become employed. Since such containers are less expensive and lighter than the collecting bottles and, in addition, are disposable, it becomes possible to dispose of collected waste liquids together with their containers. This eliminates the operations previously required to dispose of only waste liquids and wash the inside of bottles (refer to, for example, Japanese Unexamined Patent Publication No. SHO 51-48589).

However, the amount of waste liquids to be disposed of remains unvaried though the weight of the container is reduced by replacing a collecting bottle with a container of synthetic resin. Further, if one tries to incinerate a waste liquid as contained in the container using the incineration facility of a hospital, the waste liquid undesirably flows down below the incinerator with its infectiousness maintained. Thus, such incineration is difficult. After all, the process of adding an expensive microbicide to the waste liquid and draining the resultant to a sewerage system must be carried out.

In view of the fact that the greater part of the content in such container is moisture (isotonic sodium chloride solution and the like other than body fluids), a method has been employed such that a water-absorptive flocculant is provided in a container to cause the waste liquid to solidify (refer to, for example, Japanese Examined Patent Publication No. HEI 4-60713).

Although this method enables the incineration of waste liquid, substantial time and thermal energy are required to complete the incineration of the waste liquid because the thermal conductivity of the solidified waste liquid is low due to solidification. Further, not a few hospitals cannot use their incineration facilities for fear that smoke emitted by incineration should flow to residential areas. Such hospitals and those having no incineration facility are required to entrust the disposal of waste liquids to professionals of disposal. Since the overall weight of a container containing solidified waste liquid is not different from that of the foregoing container containing not solidified waste liquid, the proportion of the costs of entrusting the disposal of waste liquids in the total expenditure of a hospital is substantially high and, hence, the financial management of the hospital is oppressed.

To solve this problem, a waste liquid treating method has been proposed which is adapted to eliminate the moisture of waste liquid (refer to, for example, Japanese Examined Patent Publication No. HEI 6-36813). This prior art waste liquid treating method described in Publication No. HEI 6-36813 comprises collecting a waste liquid into a storage container by suction, eliminating the moisture of the waste liquid through a filter which is capable of filtering off infectious microbes, and disposing of the storage container having infectious microbes of the waste liquid together with the filter. This method markedly reduces the total weight and volume of the waste including the container to be disposed of as compared to the method previously described, thereby facilitating the incineration of the waste. Further, this method causes the container itself to shrink, the cost of entrusting the disposal, which depends on the weight and volume of the waste to be disposed of, can be reduced.

Japanese Unexamined Patent Publication No. HEI 1-96558 discloses another prior art technique wherein "in disposing of blood in hospitals a flocculant is added to a waste liquid to be disposed of, and the resulting mixture is stirred thereby causing almost all the blood components to flocculate".

The prior art described in Japanese Examined Patent Publication No. HEI 6-36813, however, has drawbacks that the filter may be clogged to become incapable of eliminating the moisture since microbes such as viruses, bacteria and Eumycetes existing in an infectious waste liquid are smaller than coexisting protein components such as red blood cells, that the container does not shrink as the case may be, and that the container including the filter becomes costly since the filter is expensive.

The prior art described in Japanese Unexamined Patent Publication No. HEI 1-96558 does not disclose any specific process to be performed after the separation of the waste liquid into a supernatant liquor (water content) and a flocculate (protein) and, hence, it is unclear how to treat the supernatant liquor and the flocculate for their disposal. Thus, this art is difficult to practically apply to disposal of infectious wastes. In brief this prior art merely discloses a method of separating a waste liquid, but does not disclose a method of treating the waste liquid for subjecting it to disposal.

SUMMARY OF THE INVENTION

It is, therefore, an object of the present invention to provide method and apparatus for treating a waste liquid containing body fluids which are capable of separating the waste liquid into water content and protein components and individually disposing of the separated matters with ease.

The method of treating a waste liquid containing body fluids according to the present invention comprises the steps of: collecting the waste liquid containing body fluids into a container; separating the waste liquid into a supernatant liquor and a flocculate; discharging the supernatant liquor from the container; and disposing of the flocculate remaining in the container together with the container.

In the present invention, the term "supernatant liquor" means the water content of a waste liquid, and the term "flocculate" means a flocculate of protein components of the waste liquid.

According to the present invention, a flocculant is added to the waste liquid in the step of separating the waste liquid into the supernatant liquor and the flocculate, followed by agitation. In the step of discharging the supernatant liquor it is preferable to sterilize the supernatant liquor. Further, it is preferable to cause the container to shrink in the supernatant liquor discharging step. In the step of disposing of the flocculate, it is preferable to incinerate the flocculate together with the container.

Further, in adding the flocculant to the waste liquid it is preferable to add a protein solution and an alkaline solution to the waste liquid.

The apparatus for treating a waste liquid containing body fluids according to the present invention comprises a combustible container for collecting the waste liquid therein, a separating device for separating the waste liquid into a supernatant liquor and a flocculate within the container, and a discharging device for discharging the supernatant liquor from the container.

The container is preferably portable and deformable. The separating device has a flocculant adding device for adding a flocculant to the waste liquid. The separating device further has an agitating device for agitating the waste liquid admixed with the flocculant.

The discharging device is preferably adapted to cause the container to shrink so as to discharge the supernatant liquor from the container. The discharging device has either a suction device for aspirating the supernatant liquor from the container or a pressure device for forcing the supernatant liquor out of the container. The discharging device preferably further has a sterilizing device for sterilizing the supernatant liquor.

The sterilizing device preferably comprises a heating device for heating the supernatant liquor or a hemolysis causing device for causing hemolysis of red blood cells contained in the supernatant liquor.

According to the present invention thus constructed, the waste liquid containing body fluids such as blood and an irrigation liquid used to irrigate the body cavity of a patient is collected into the container, and then the separating device separates the waste liquid into the supernatant liquor and the flocculate within the container.

Where the separating device comprises the flocculant adding device and the agitating device, the flocculant adding device adds the flocculant to the waste liquid collected in the container and then the agitating device agitates the resulting mixture, so that cellular components of blood such as red blood cells as well as the protein components (albumin and the like) contained in blood plasma which is the liquid component of blood are flocculated and precipitated thereby allowing the separation of the flocculate from the supernatant liquor to occur with ease.

The supernatant liquor thus separated of the waste liquid is discharged, front the container by the discharging device and then treated for disposal, while the flocculate remaining in the container is subjected to incineration disposal together with the container.

More specifically, the supernatant liquor in the container is discharged from the container by the suction device or the pressure device and then heat-sterilized by the sterilizing device comprising the heating device, followed by its disposal. If the hemolysis causing device is used in the sterilizing process to cause hemolysis of red blood cells contained in the supernatant liquor, sterilization would be more reliably achieved.

According to the present invention, the separation of the waste liquid into the supernatant liquor and the flocculate can be achieved with ease. Further, since the waste liquid is subjected to disposal after the supernatant liquor is sterilized or disinfected to kill viruses and microbes contained therein, it is possible to prevent secondary infection to the surroundings of the waste liquid such as personnel engaged in medical treatments and other patients. Furthermore, since only the supernatant liquor separated in the container is discharged, and then the container is caused to shrink for minimizing the volume thereof, it is possible to reduce the cost of entrusting the waste to professionals of disposal or ease the incineration of the waste in a hospital.

Thus, the present invention makes it possible to realize a safe and less costly disposal treatment.

DESCRIPTION OF THE PREFERRED EMBODIMENTS

When a waste liquid containing body fluids collected from a patient under surgical operation or treatment such as blood and an irrigation liquid used to irrigate the body cavity of the patient is admixed with a flocculant, red blood cells contained in the waste liquid are mostly flocculated and precipitated into a flocculate, while blood plasma components together with the rest of red blood cells are suspended in the supernatant liquor.

The amount of the flocculant to be used is determined based on the concentration of blood in the waste liquid.

Waste liquids discharged from (surgical) operating rooms generally comprise blood and a body cavity irrigation liquid (isotonic sodium chloride solution). The blood concentration of such waste liquids is presumably about 10%, but is not constant. Experiments carried out by the inventors of the present invention revealed that addition of any amount of flocculant to a waste liquid having a very low blood concentration did not cause blood components to flocculate.

For this reason, in the present invention a protein solution is added to a waste liquid so that the concentration of flocculatable substances in the waste liquid should assume a value equal to or higher than a predetermined value. Further, an alkaline solution is added to the waste liquid to facilitate flocculation.

According to the following experiments carried out by the inventors, the amount of protein contained in the supernatant liquor of a waste liquid tended to be considerably low compared to that contained in the waste liquid before being admixed with the flocculant.

In the first experiment waste liquids having different blood concentrations were admixed with the flocculant in a constant amount, while in the second experiment the flocculant in a varying amount was added to two types of waste liquids having blood concentrations different from each other.

In the first experiment, blood was mixed with isotonic sodium chloride solution to prepare five types of waste liquids having blood concentrations of 1%, 3%, 5%, 10% and 30%, respectively. (The amount of each waste liquid was 100 cc.) The number of red blood cells contained in each waste liquid in this condition was determined. The number thus determined is herein referred to as the initial number of red blood cells. To each waste liquid was then added 4 cc of a protein solution, 17 cc of the flocculant (tradename "HIGHSET C-200" available from DAIICHI KOGYO SEIYAKU Co., Ltd.), and 0.6 cc of an alkaline solution in this order. The resulting waste liquid was agitated for three minutes using a stirrer at 300 rpm, and then allowed to stand for seven minutes. The amounts of the resulting supernatant liquor and flocculate (precipitate) and the number of red blood cells contained in the supernatant liquor were measured. The results of the first experiment are shown in Table 1.

TABLE 1

| A* (%) | B* (cc) | C* (cc) | D* (cells/cc) | E* (cells/cc) |
|---|---|---|---|---|
| 1 | 115 | 6 | 9.5E + 07 | less than 1.0E + 04 |
| 3 | 112 | 9 | 3.0E + 08 | 9.3E + 04 |
| 5 | 112 | 9 | 5.5E + 08 | 4.5E + 05 |
| 10 | 112 | 9 | 8.6E + 08 | 1.3E + 06 |
| 30 | 98 | 23 | 2.6E + 09 | 3.3E + 04 |

Note:
A* = Blood concentration of waste liquid
B* = Amount of supernatant liquor obtained after flocculation
C* = Amount of precipitate obtained after flocculation
D* = Initial number of red blood cells
E* = Number of red blood cells contained in supernatant liquor obtained after flocculation In the second experiment, blood was mixed with isotonic sodium chloride solution to give two types of waste liquids having blood concentrations of 10% and 30%, respectively. (The amount of each waste liquid was 100 cc.) The number of red blood cells contained in each waste liquid in this condition was determined as the initial number of red blood cells. The initial number of red blood cells contained in each 10% blood waste liquid thus determined was 5.4E+08 cells/cc, and that of blood cells contained in each 30% blood waste liquid was 2.2E+09 cells/cc.

Subsequently, the flocculant in a varying amount as shown in Tables 2 and 3 was added to the waste liquids, and the resulting waste liquids were agitated for about 3 minutes with the stirrer. The waste liquids thus agitated were allowed to stand for seven minutes thereby separating each waste liquid into a supernatant liquor and a flocculate (precipitate). The number of red blood cells contained in the supernatant liquor thus obtained was determined, and the results are shown in Tables 2 and 3.

TABLE 2

10% Blood Waste Liquids (Volume: 100 cc)

| A* (cc) | B* (cc) | C* (cc) | D* (cells/cc) | E* (cells/cc) |
|---|---|---|---|---|
| 1 | not flocculated | not flocculated | 5.4E + 08 | not flocculated |
| 3 | 95 | 8 | " | 3.9E + 05 |
| 5 | 97 | 8 | " | 4.3E + 05 |
| 7 | 99 | 8 | " | 5.9E + 05 |
| 8 | 100 | 8 | " | 4.7E + 05 |
| 9 | 99 | 10 | " | 6.6E + 05 |
| 10 | 100 | 10 | " | 7.0E + 05 |
| 15 | 105 | 10 | " | 2.6E + 06 |
| 20 | 105 | 15 | " | 3.9E + 06 |

Note:
A* = Amount of flocculant added
B* = Amount of supernatant liquor obtained after flocculation
C* = Amount of precipitate obtained after flocculation
D* = Initial number of red blood cells
E* = Number of red blood cells contained in supernatant liquor obtained after flocculation

TABLE 3

30% Blood Waste Liquids (Volume: 100 cc)

| A* (cc) | B* (cc) | C* (cc) | D* (cells/cc) | E* (cells/cc) |
|---|---|---|---|---|
| 3 | not flocculated | not flocculated | 2.2E + 09 | not flocculated |
| 4 | not flocculated | not flocculated | " | not flocculated |
| 5 | not flocculated | not flocculated | " | not flocculated |
| 6 | 81 | 25 | " | — |
| 7 | 82 | 25 | " | — |
| 8 | 83 | 25 | " | — |
| 9 | 84 | 25 | " | 8.4E +06 |
| 10 | 85 | 25 | " | 4.0E +05 |
| 15 | 90 | 25 | " | 2.7E +05 |
| 20 | 95 | 25 | " | 1.1E +05 |
| 25 | 100 | 25 | " | 8.3E +04 |
| 30 | 105 | 25 | " | 1.2E +04 |
| 35 | 110 | 25 | " | 6.5E +04 |
| 40 | 115 | 25 | " | 3.0E +04 |

Note:
A* = Amount of flocculant added
B* = Amount of supernatant liquor obtained after flocculation
C* = Amount of precipitate obtained after flocculation
D* = Initial number of red blood cells As seen from Tables 1 to 3, addition of the flocculant to each waste liquid allowed a supernatant liquor containing a considerably reduced amount of protein to be obtained. In such supernatant liquor the effectiveness of a disinfectant is less likely to degrade, thus facilitating sterilization or disinfection.

Preferably, such disinfectant is added directly to the supernatant liquor. Examples of preferred disinfectants include hydrogen peroxide solution, sodium hypochlorite solution, glutaraldehyde, benzalkonium chloride, benzethonium chloride, chlorhexidine gluconate, alkyldiaminoethylglycine, and anionic or cationic surface active agents. Alternatively, water is added to the supernatant liquor to cause hemolysis or destruction of blood cells suspended therein, thereby releasing substances containing viruses or other infectious microbes from the blood cells, followed by sterilization or disinfection using appropriate disinfectants or by a heat treatment. Since viruses or certain kinds of bacteria and Eumycetes may live in blood cells, such hemolysis causing process achieves more reliable sterilization or disinfection.

Further, the following test conducted by the inventors has discovered the fact that polymer flocculants adapted to cause organic matters such as protein to flocculate are capable of causing flocculation and precipitation of not only blood cell components but also microbes contained in infectious waste blood collected during a surgical operation.

Figure 9:
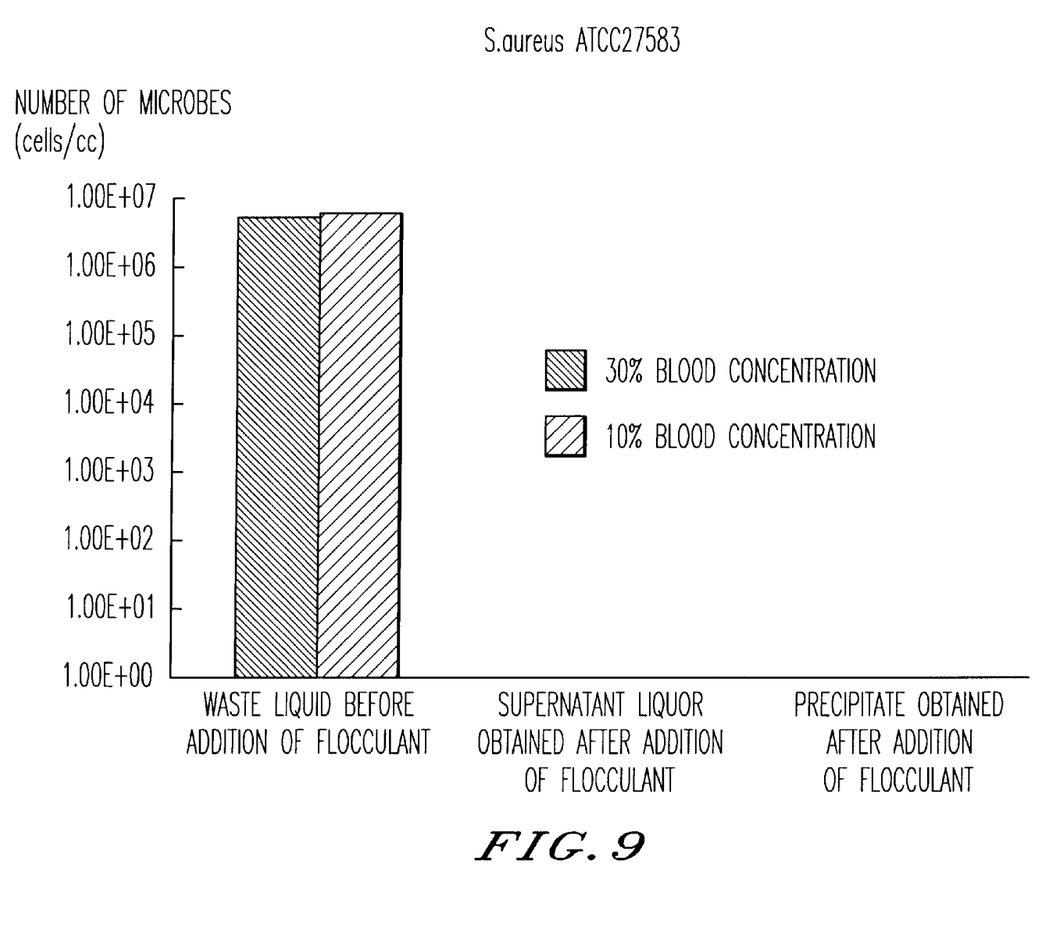
FIG. 9 is a graph showing the results of a determination of the number of microbes.
Figure 10:
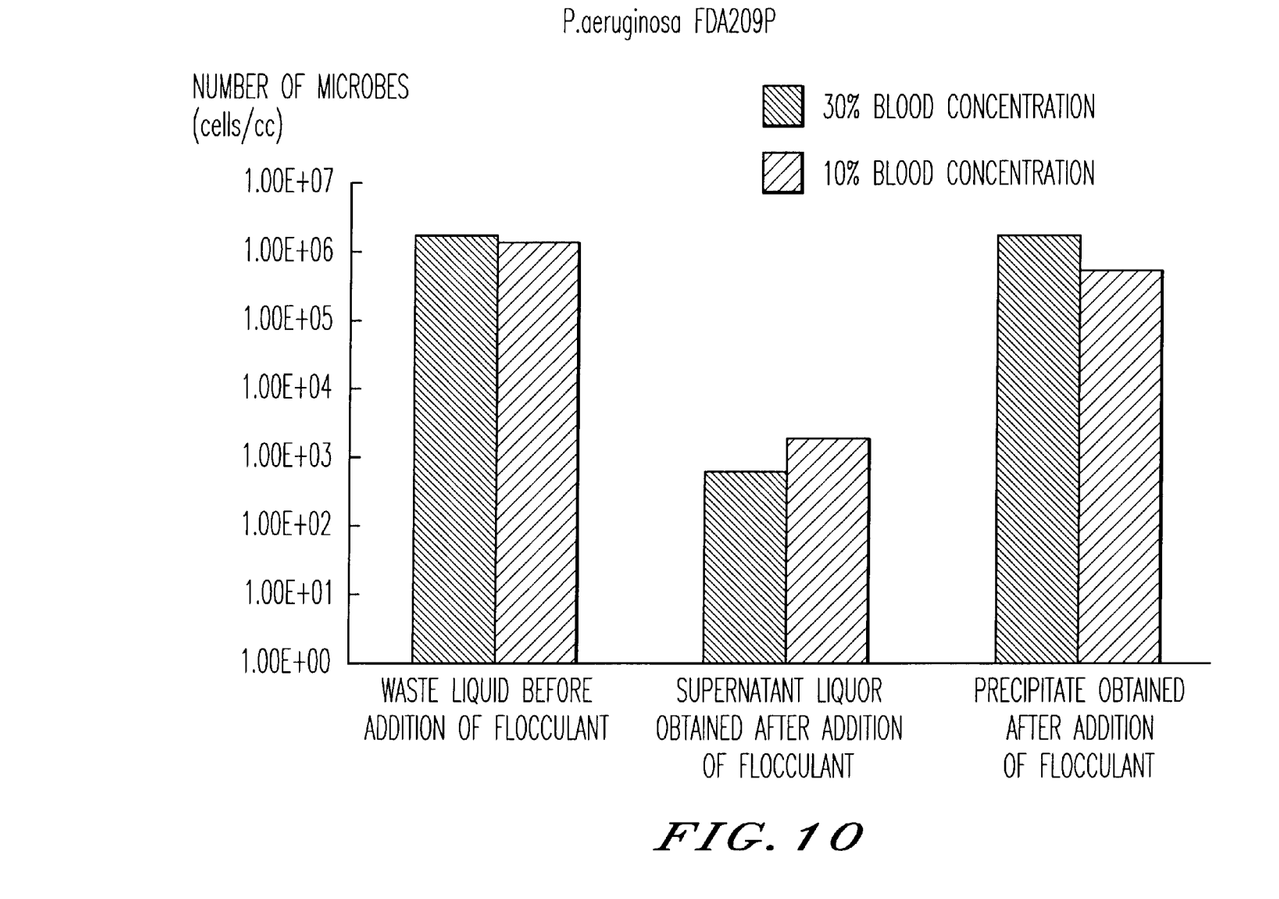
FIG. 10 is a graph showing the results of a determination of the number of microbes.

Specifically, blood was mixed with isotonic sodium chloride solution to afford two types of waste liquids having blood concentrations of 10% and 30%, respectively. Each waste liquid was added with *Staphylococcus aureaus* or *Pseudomonas aeruginosa* and then agitated with a stirrer. The number of microbes contained in the waste liquid thus agitated was determined. The results are shown as Number of microbes before addition of flocculant in Tables 4 and 5 and FIGS. 9 and 10.

Subsequently, the waste liquid was admixed with a flocculant and agitated for about three minutes, and then allowed to stand for seven minutes for separation into a supernatant liquor and a flocculate (precipitate). The number of microbes contained in each of the resulting supernatant liquor and flocculate was determined. The results of the determination are shown in Table 4 and 5 and FIGS. 9 and 10.

TABLE 4

*S. aureus* ATCC27583

| | B* | | |
|---|---|---|---|
| A* | C* | D* | E* |
| 30 | 5.6E + 06 | 0 | 0 |
| 10 | 6.1E + 06 | 0 | 0 |

Note:
A* = Blood concentration (%)
B* = Number of microbes (cells/cc)
C* = Waste liquid before addition of flocculant
D* = Supernatant liquor obtained after addition of flocculant
E* = Precipitate obtained after addition of flocculant

TABLE 5

*P. aeruginosa* FDA209P

| | B* | | |
|---|---|---|---|
| A* | C* | D* | E* |
| 30 | 1.9E + 06 | 7.8E + 02 | 1.8E + 06 |
| 10 | 1.6E + 06 | 2.0E + 03 | 5.2E + 05 |

Note:
A* = Blood concentration (%)
B* = Number of microbes (cells/cc)
C* = Waste liquid before addition of flocculant
D* = Supernatant liquor obtained after addition of flocculant
E* = Precipitate obtained after addition of flocculant As clearly seen from Tables 4 and 5 and FIGS. 9 and 10, *Staphylococcus aureaus* was found to no longer exist in any of supernant liquor and flocculate obtained after the addition of flocculant, and *Pseudomonas aeruginosa* was found to be largely flocculated into the flocculate.

This flocculation of microbes provides an advantage that the total amount of organic matters existing in the supernatant liquor is substantially reduced before sterilization so that the sterilization by heating or with a disinfectant is facilitated. Further, the time required for the heat sterilization can be shortened, or alternatively the concentration or amount of the disinfectant to be required can be reduced since the sterilization is hardly affected by the influence of organic matters in the supernatant liquor.

Hereinafter, a more specific mode for carrying out the present invention will be described with reference to the drawings.

Figure 1:
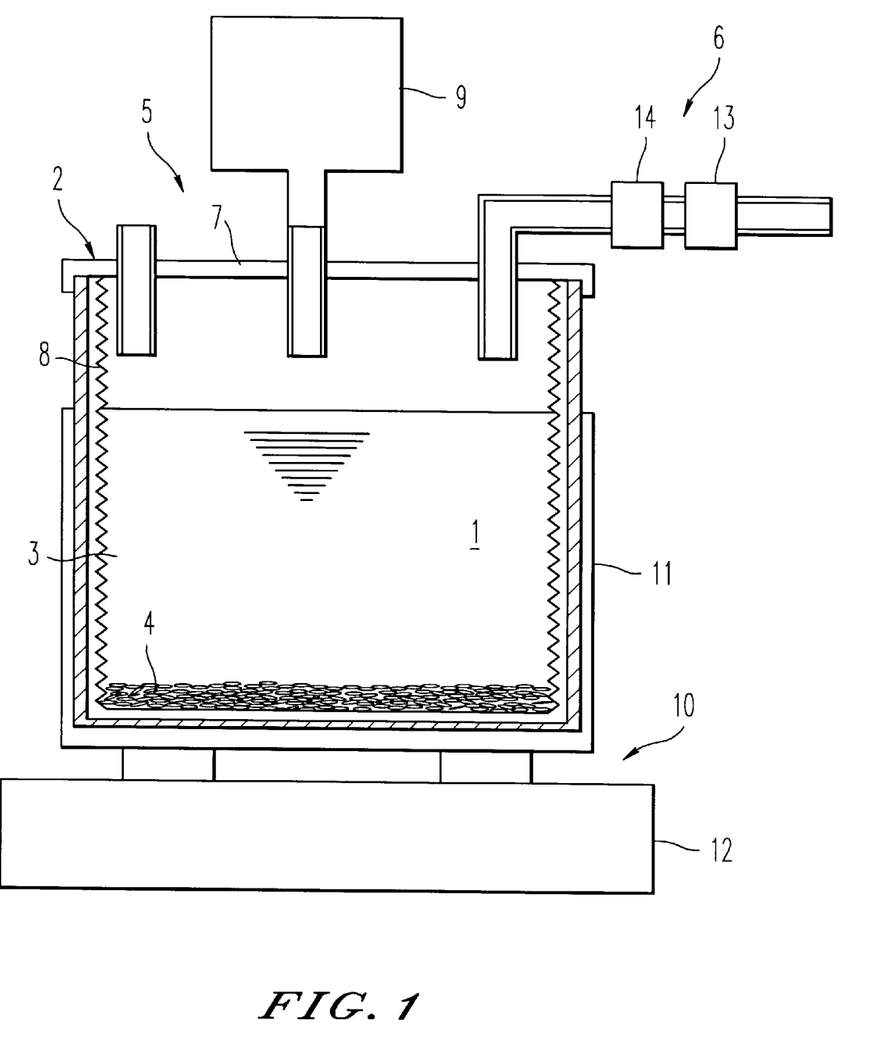
FIG. 1 is a schematic illustration showing a mode for carrying out the present invention.

Referring to FIG. 1, apparatus for treating a waste liquid containing body fluids according to the present invention includes a waste liquid container 2 for collecting therein a waste liquid 1 containing body fluids, a separating device 5 for separating the waste liquid 1 in the waste liquid container 2 into a supernatant liquor 3 and a flocculate 4, and a discharging device 6 for discharging the supernatant liquor 3 from the container 2.

The waste liquid container 2 is sized to be carried by a human (having a capacity of collecting about 2 to about 10 liters of a waste liquid), and is combustible and deformable. More specifically, the waste liquid container 2 is formed of a soft plastic and comprises a top lid 7 and a bag 8 coupled to the top lid 7. The bag 8 is flexible and deformable, while the top lid 7 is formed thick and difficult to deform.

The separating device 5 has a flocculant adding device 9 for introducing a flocculant into the waste liquid container 2. The flocculant adding device 9 is removably connected to the top lid 7 of the waste liquid container 2. The separating device 5 further has an agitating device 10 for agitating the waste liquid 1 added with the flocculant in the container 2. The agitating device 10 comprises a holder 11 for holding the waste liquid container 2 in an upright condition, and a vibrator 12 for vibrating the holder 11.

The agitating device 10 may employ, instead of the vibrator 12, a stirrer or a shaker to agitate the waste liquid 1 in the waste liquid container 2. If the stirrer is used, a stirring bar is required to be provided within the container 2.

The discharging device 6 is removably connected to the top lid 7 of the waste liquid container 2, and includes a suction device 13 for aspirating the supernatant liquor 3 from the container 2 and a sterilizing device 14 for sterilizing the supernatant liquor 3. The sterilizing device 14 may comprise a heating device for achieving sterilization by heating.

The sterilization may be achieved by adding a disinfectant to the flocculant to be added to the waste liquid 1.

With the waste liquid treating unit thus constructed, the waste liquid 1 containing body fluids, body cavity irrigation liquid and the like is collected into the waste liquid container 2 by suction, and then the container 2 is held by the holder 11 of the separating device 5. In turn, the flocculant adding device 9 and the discharging device 6 are connected to the container 2.

Subsequently, the flocculant adding device 9 supplies into the container 2 the flocculant (polymer flocculant capable of flocculating protein components), followed by agitation with the agitating device 10. The resulting waste liquid 1 is allowed to stand for a predetermined period of time to cause cell components, such as red blood cells, of the blood and protein components, such as albumin, of the blood plasma to flocculate and precipitate, thereby separating the waste liquid 1 into the supernatant liquor 3 and the flocculate 4.

In turn, only the supernatant liquor 3 thus separated of the waste liquid 1 is then discharged from the container 2 by means of the suction device 13 of the discharging device 6 and, simultaneously, sterilized by heating or with the disinfectant utilizing the disinfecting effect of the disinfectant or the hemolysis of red blood cells due to addition of water. Thereafter, the supernatant liquor 3 thus sterilized is disposed of by draining it to a sewerage system. On the other hand, the flocculate 4 precipitated in the bottom portion of the waste liquid container 2 together with the container 2 is disposed of by incineration or entrusted to professionals of disposal.

EMBODIMENTS

The embodiments of the present invention will hereinafter be described with reference to the drawings. It should be noted that elements of these embodiments corresponding to those of the foregoing specific mode are designated by like reference numerals.

Figure 2:
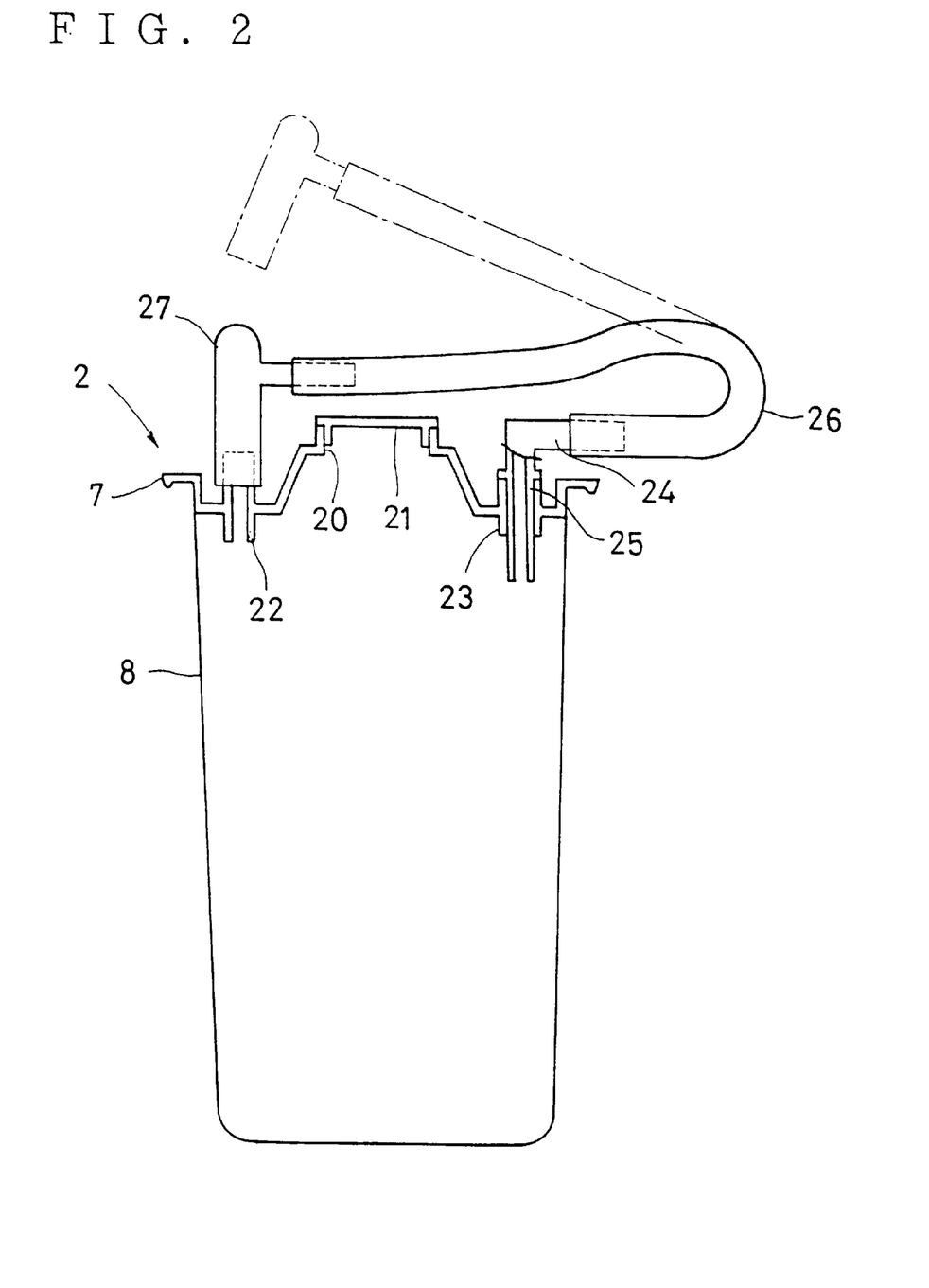
FIG. 2 is a partially sectional view of a waste liquid collecting container.

FIG. 2 illustrates a waste liquid container 2 comprising a thick top lid 7 of plastic and a thin bag 8 of soft plastic in the form of a bottomed cylinder, the bag 8 being hermetically joined integrally with the top lid 7 by fusion bonding or adhesive bonding. The bag 8 is of a portable size and is flexible, deformable and combustible since it is made thin. Even if the bag 8 is thick, it becomes easy to deform by molding it into a bellows configuration.

The top lid 7 centrally defines an opening 20 into which a blank cap 21 is removably fitted. The blank cap 21 maintains hermetic seal of the waste liquid container 2.

The top lid 7 further has an inlet port 22 and an outlet port 23 which are formed integrally with the top lid 7. Into the outlet port 23 is rotatably inserted a first elbow 24 through a seal part 25. The first elbow 24 is connected to a pipe of vinyl 26, which, in turn, is connected at its other end to a second elbow 27. The second elbow 27, when not in use, is removably fitted over the inlet port 22 to ensure the hermetic closure of the container 2.

The second elbow 27, when to be used, is removed from the inlet port 22 and connected to the suction device not shown. The inlet port 22 from which the second elbow 27 is removed is connected to a waste liquid suction tube (not shown) associated with a (surgical) operating table or the like. The suction device (not shown) then sucks waste liquid 1 containing body fluids discharged from a patient under (surgical) operation or medical treatment to collect it into the bag 8 of the waste liquid container 2 through the inlet port 22. After the suction is completed, the waste liquid suction tube is detached from the inlet port 22, and the second elbow 27 is removed from the suction device and then fitted over the inlet port 22. Thus, the hermetic closure of the waste liquid container 2 is recovered.

The waste liquid 1 thus collected is treated by the following waste liquid treating unit.

Figure 3:
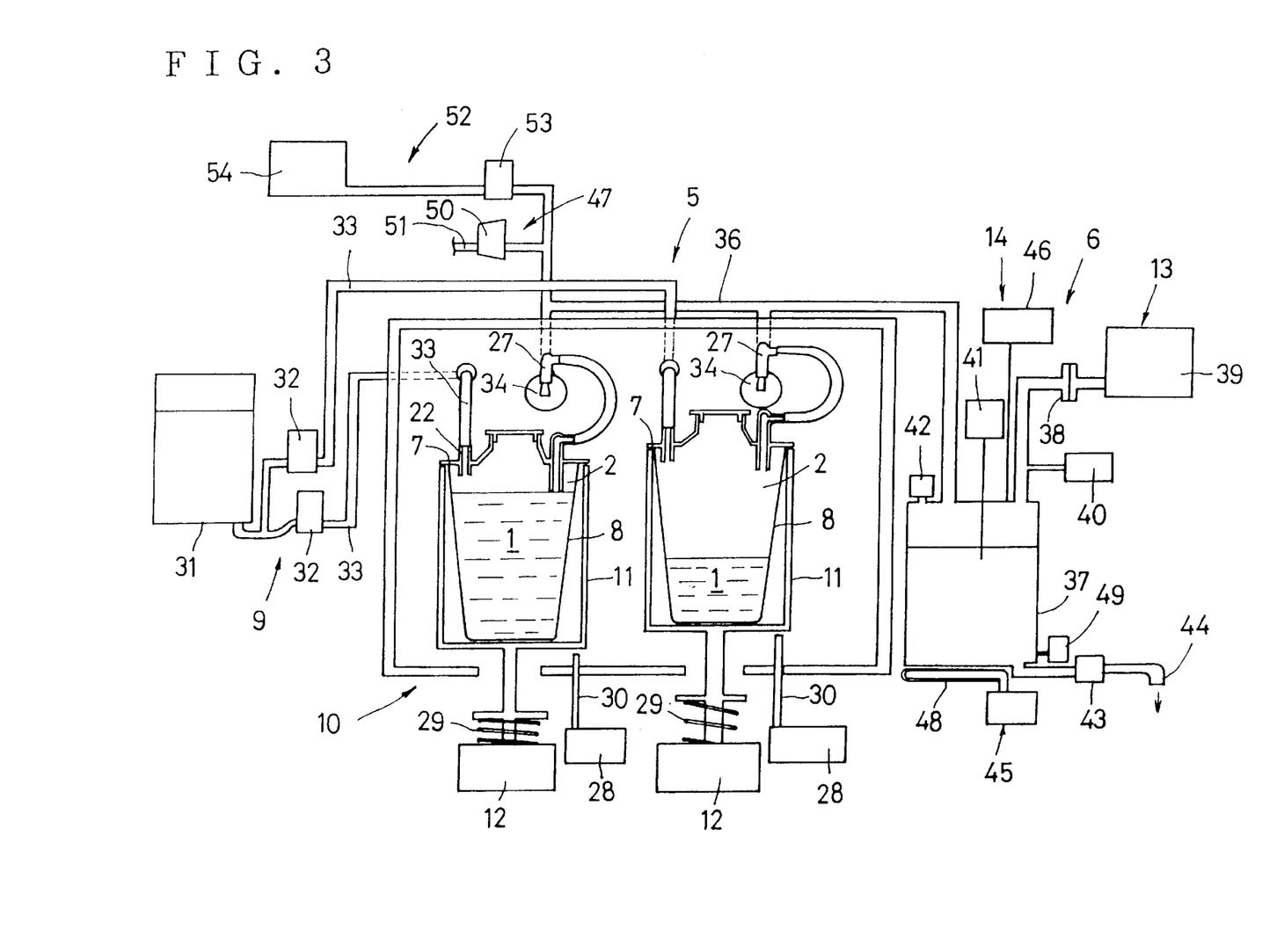
FIG. 3 is a schematic illustration showing the construction of an embodiment of the present invention.

The waste liquid treating unit shown in FIG. 3 comprises a separating device 5 for separating the waste liquid 1 in the waste liquid container 2 into a supernatant liquor 3 and a flocculate 4, and a discharging device 6 for discharging the supernatant liquor 3 from the container 2.

The separating device 5 includes a flocculant adding device 9 for adding a flocculant to the waste liquid 1, and an agitating device 10 for agitating the waste liquid 1 added with the flocculant.

In association with the flocculant adding device 9 and agitating device 10 a single or plural cylindrical holders 11 having open top are provided for holding the bag 8 in a suspended fashion by supporting the top lid 7 of the waste liquid container 2. Each holder 11 is provided with a liquid quantity sensor 28 for measuring the quantity of the waste liquid 1 contained in the container 2. Specifically, the measurement of the quantity of the waste liquid 1 in the container 2 is achieved such that the liquid quantity sensor 28 measures the amount of move of a sensor probe 30 adapted to measure the amount of deformation of a spring 29 which elastically supports the holder 11. The holder 11 is connected to a vibrator 12 which vibrates the holder 11 in vertical or horizontal directions or composite directions thereof so as to agitate the waste liquid 1 added with the flocculant in the container 2.

The flocculant adding device 9 has a flocculant tank 31 storing the predetermined flocculant for causing the waste liquid 1 to be separated into the supernatant liquor 3 and the flocculate 4. The tank 31 is connected to a flocculant supply pump 32, which in turn is connected at its outlet to a flocculant supply tube 33. The other end of the flocculant supply tube 33 is so constructed as to removably connect to the inlet port 22 of the waste liquid container 2.

The pump 32 and the liquid quantity sensor 28 are electrically connected to each other through a control device (not shown) so that an optimum amount of the flocculant relative to the measured quantity of the waste liquid 1 in the container 2 can be automatically supplied to the waste liquid 1 through the pump 32. Accordingly, the number of flocculant supply pumps 32 provided is equal to the number of holders 11. The pump 32 is of the tubular type or a like type which, when halted, tightly shuts off the communication between the tank 31 side and the flocculant supply tube 33 side.

The discharging device 6 includes a suction device 13 for sucking the supernatant liquor 3 from the waste liquid container 2, and a sterilizing device 14 for sterilizing the supernatant liquor 3.

Figures 4A, 4B:
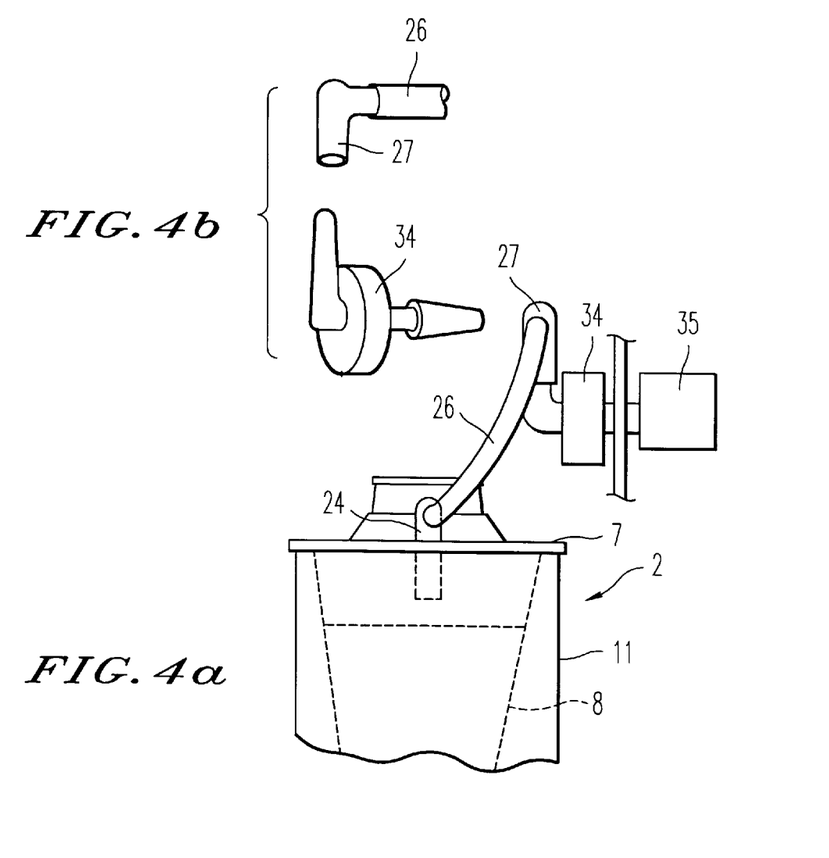
FIG. 4 is an explanatory view showing a connection structure between a waste liquid collecting container and a discharging device.

The suction device 13 has a filter 34 removably connected to the second elbow 27 of the container 2 which, in turn, is connected to a waste liquid sucking tube 36 through a coupler 35 (see FIG. 4). The coupler 35 is so constructed as to open its passage when connected to the filter 34 and to close the passage when released from the filter 34. The waste liquid sucking tube 36 in turn is connected to a treatment vessel 37 having a top cover connected to a vacuum pump 39 through a flow stopper 38. In this embodiment is used as the flow stopper 38 that described in Japanese Unexamined Patent Publication No. HEI 5-201452. The filter 34 need not necessarily have a mesh fine enough to prevent red blood cells from passing threrethrough but is required to prevent the flocculate 4 from passing therethrough. The filter 4 is preferably a disposable one comprising wire gauze, absorbent cotton or the like.

In the course of the suction path is provided a pressure sensor 40 for causing the vacuum pump 39 to stop when the negative pressure for suction exceeds a predetermined value. The treatment vessel 37 is provided with a water level sensor 41 for causing the vacuum pump 39 to stop when the level of the supernatant liquor 3 collected into the treatment vessel 37 exceeds a predetermined value. The treatment vessel 37 is further provided with an air vent valve 42 and is connected to a drain tube 44 through a drain valve 43 at the bottom thereof.

The sterilizing device 14 includes a heating device 45 for heating the supernatant liquor 3 in the treatment vessel 37, a microbicide adding device 46 for adding a microbicide to the supernatant liquor 3 in the treatment vessel 37, and a hemolysis causing device 47 for causing hemolysis of red blood cells.

The heating device 45 includes a heater 48 adapted to heat the supernatant liquor 3 in the treatment vessel 37, and a temperature sensor 49 for measuring the temperature of the supernatant liquor 3 in the treatment vessel 37. The microbicide adding device 46 is connected to the top cover of the treatment vessel 37 to feed the microbicide into the treatment vessel 37. The hemolysis causing device 47 causes hemolysis of red blood cells by diluting the supernatant liquor 3 with water and comprises a water tank or water pipe 51 connected to the waste liquid sucking tube 36 through a washing valve 50.

The discharging device 6 is associated with a washing device 52 including a washing and sterilizing tank 54 connected to the waste liquid sucking tube 36 through a washing and sterilizing valve 53. The washing and sterilizing tank 54 stores a washing and sterilizing liquid containing a proteolytic enzyme.

The waste liquid treatment using the waste liquid treating unit thus constructed is carried out in the following procedure.

The waste liquid container 2 containing waste liquid 1 is secured on the holder 11 of the separating device 5. Since the edge of the top lid 7 of the container 2 is securely fixed to the top portion of the holder 11, the bag 8 of the container 2 is held in a suspended fashion. Then, the second elbow 27 is removed from the inlet port 22 and connected to the filter 34 of the discharging device 6 as shown in FIG. 4. The inlet port 22 in turn is connected to the flocculant supply tube 33.

When an operation start switch is turned on, the liquid quantity sensor 28 measures the quantity of waste liquid 1 in the waste liquid container 2. The result of the measurement is transmitted through the control device to the flocculant supply pump 32 as an actuation directive value thereby supplying an appropriate amount of flocculant relative to the quantity of the waste liquid 1 into the waste liquid container 2. The amount of flocculant to be supplied is controlled by controlling the operation time of the pump 32, but not limited thereto. This may otherwise be achieved by controlling the time period of maintaining the open state of an associated valve or by other various flow control techniques.

Once the appropriate amount of flocculant is supplied, the vibrator 12 is automatically actuated to agitate the waste liquid 1 added with the flocculant in the container 2. The operation time of the vibrator 12 may be made constant by being controlled with a timer or the like, or may be made variable by being automatically controlled depending on the quantity of waste liquid 1 or the like.

Figures 5A, 5B:
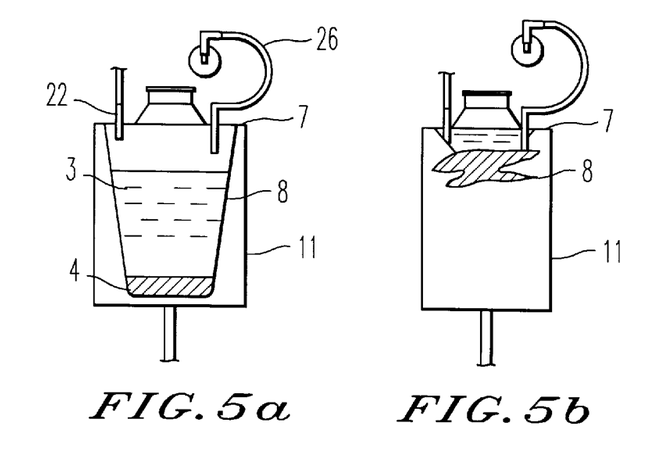
FIG. 5 is an explanatory view showing a procedure of treating a waste liquid according to the present invention.

The waste liquid 1 is then allowed to stand for a predetermined time so as to be separated into supernatant liquor 3 and flocculate 4. Thereafter the vacuum pump 39 is automatically actuated to aspirate air and supernatant liquor 3 from the waste liquid container 2. The supernatant liquor 3 thus aspirated is collected into the treatment vessel 37. At this time the bag 8 deflates or shrinks due to negative pressure and the supernatant liquor 3 is mostly withdrawn from the container 2 by suction as shown in FIG. 5(*b*). When the bag 8 shrinks to a limit, the negative pressure within the treatment vessel 37 rises and, in response thereto, the pressure sensor 40 is actuated to cause the vacuum pump 39 to stop operating.

In case the flocculate 4 begins to be withdrawn before the bag 8 reaches its shrinkage limit, the flocculate 4 arrives at the filter 34 and occludes the filter 34 thereby raising the negative pressure in the treatment vessel 37. This causes the pressure sensor 40 to be actuated to stop the operation of the vacuum pump 39.

In response to the stop operating of the vacuum pump 39, the air vent valve 42 is opened thereby causing supernatant liquor 3 in the waste liquid sucking tube 36 to flow into either the waste liquid container 2 or the treatment vessel 37. Thus, the supernatant liquor 3 will not remain in the sucking tube 36. This avoids scattering of the supernatant liquor 3 when the filter 34 is removed from the coupler 35.

Figure 5C:
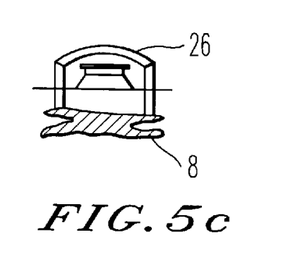

Subsequently, the second elbow 27 is detached from the filter 34 and fitted into the inlet port 22, and then the waste liquid container 2 in a shrunk state as shown in FIG. 5(*c*) together with the flocculate 4 therein is disposed of by incineration. The filter 34 thus removed from the apparatus is also subjected to incineration. Since the waste liquid container 2 is extremely reduced in volume as shown in FIG. 5(*c*), the container 2 containing the flocculate 4 is easy to incinerate while requiring a reduced cost of its disposal.

On the other hand, the supernatant liquor 3 collected into the treatment vessel 37 is supplied with water from the hemolysis causing device 47 so as to be diluted, thereby causing hemolysis of residual red blood cells suspended in the supernatant liquor 3. The hemolysis of residual red blood cells enhances the sterilization of the supernatant liquor 3. More specifically, the addition of water to the supernatant liquor 3 makes it possible to cause hemolysis of the residual red blood cells suspended therein, so that viruses and microbes living in the red blood cells are released therefrom, thus ensuring reliable sterilization. Subsequently, the supernatant liquor 3 thus diluted is added with a predetermined amount of a microbicide fed from microbicide adding device 46 and then heated by the heating device 45 to achieve sterilization. After completion of the sterilization the drain valve 43 is opened to drain the thus sterilized waste liquid to a sewerage system or the like through the drain tube 44.

The circuit including the waste liquid sucking tube 36 and the like is washed and sterilized by feeding a washing/sterilizing liquid into the circuit by opening the valve 53 manually or automatically.

Figure 6:
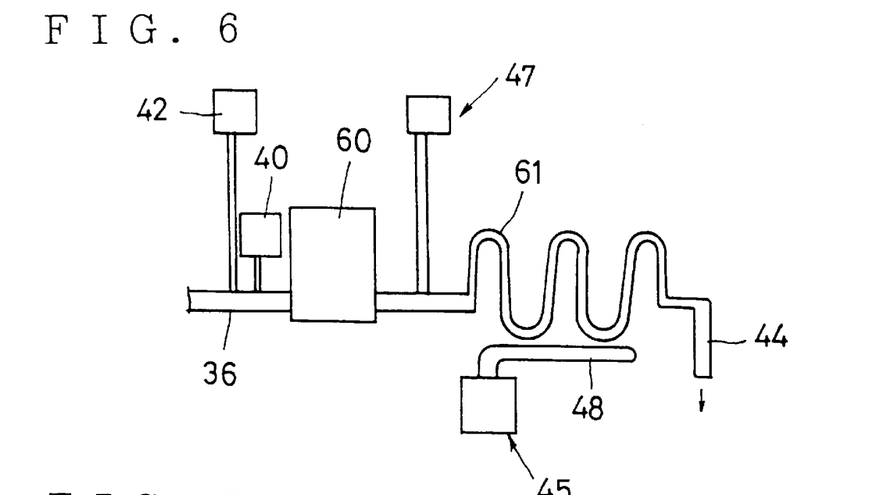
FIG. 6 is a schematic illustration showing a partial construction of another embodiment of the present invention.

FIG. 6 shows another embodiment of the present invention in which supernatant liquor 3 is continuously sterilized by heating while being collected from the waste liquid container, unlike the foregoing embodiment wherein the supernatant liquor 3 is provisionally collected in the treatment vessel so as to be treated therein.

A waste liquid sucking tube 36 is connected to a discharge pump 60 adapted to suck and eject the supernatant liquor 3. On the outlet side of the pump 60 are provided a heating pipe 61 and a heater 48 for heating the heating pipe 61. The downstream side of the heating pipe 61 is connected to a drain tube 44 for draining the supernatant liquor 3 to a sewerage system. To the upstream side of the heating pipe 61 is connected a hemolysis causing device 47 adapted to supply water to the supernatant liquor 3 for dilution.

A pressure sensor 40 and an air vent valve 42 are connected to the waste liquid sucking tube 36 upstream of the discharge pump 60.

Thus, the apparatus shown in FIG. 6 enables continuous sterilization of supernatant liquor 3.

Figure 7:
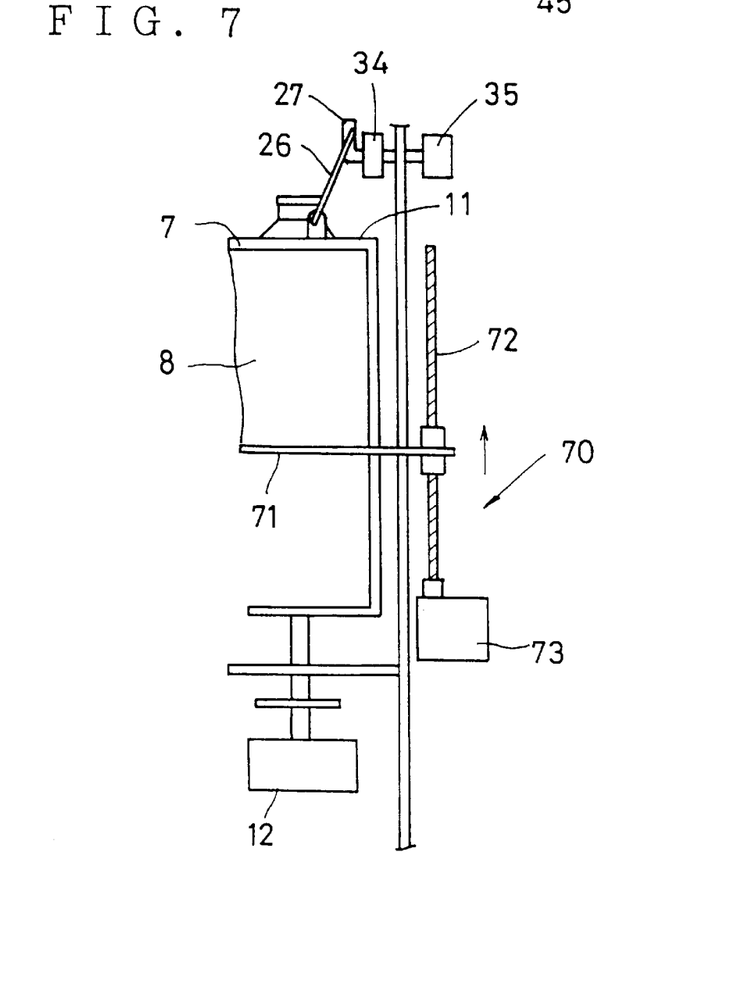
FIG. 7 is a schematic illustration showing a partial construction of another embodiment of the present invention.

FIG. 7 shows yet another embodiment of the present invention which employs a pressure device 70 as the discharging device 6. The pressure device 70 comprises a press-up part 71 vertically movably mounted on holder 11 for pressing up the bottom of bag 8 of waste liquid container 2. The vertical movement of the press-up device 71 is achieved through a raising/lowering screw 72, which in turn is driven by a motor 73 for rotation.

The provision of the pressure device 70 dispenses with the vacuum pump 39 as shown in FIG. 3 or the discharge pump 60 as shown in FIG. 6.

Figure 8:
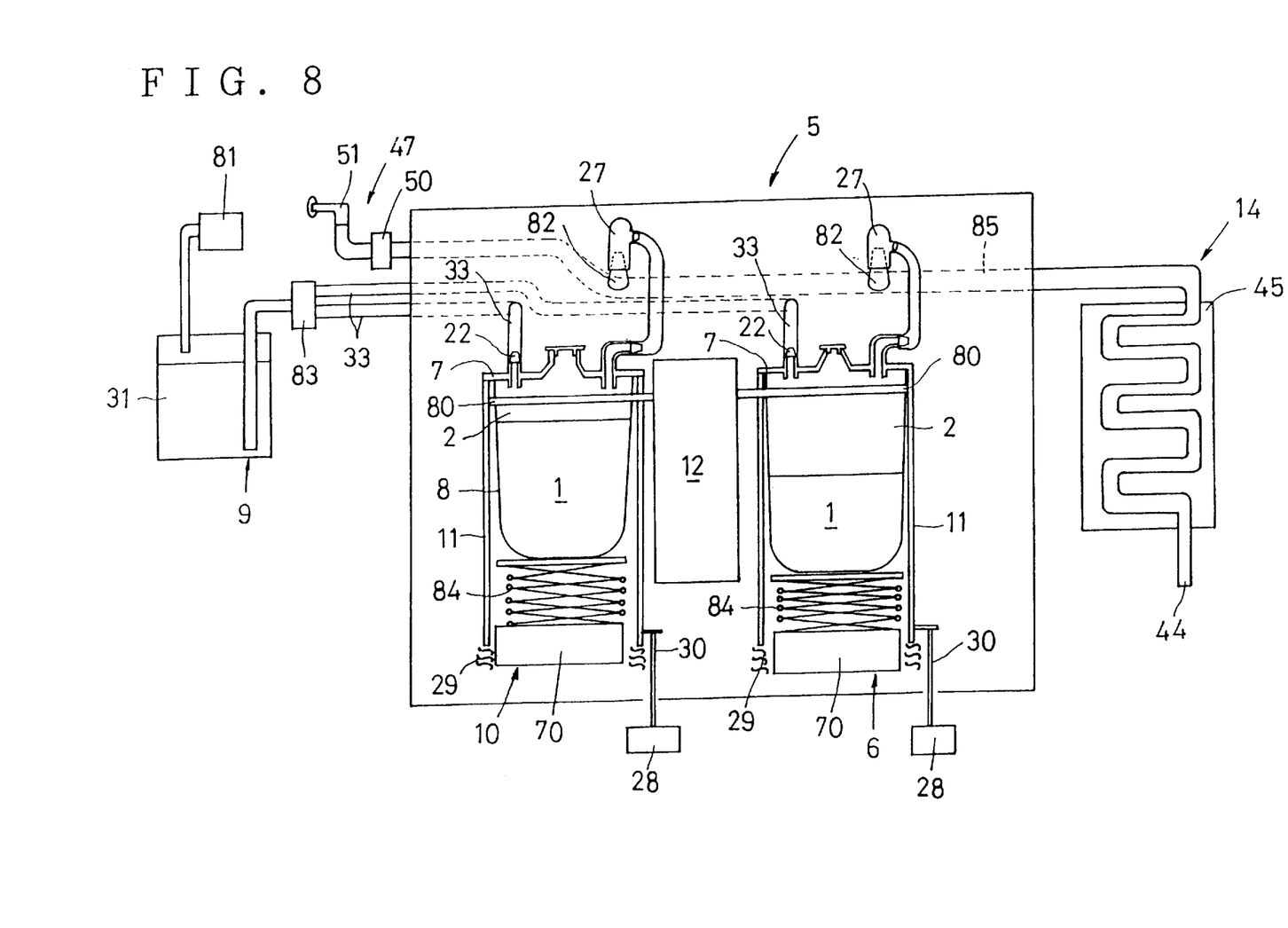
FIG. 8 is a schematic illustration showing another embodiment of the present invention.

FIG. 8 shows still another embodiment of the present invention.

With this embodiment, the waste liquid container 2 is set on bottomless holder 11. In this case the top lid 7 of the container 2 is firmly secured to the holder 11, while the body of the container 2 is firmly fastened by an agitation belt 80.

When the container 2 is set on the holder 11, the weight of waste liquid 1 contained therein causes the holder 11 to be pressed downward. This in turn causes a compression spring 29 to be compressed, hence, a sensor probe 30 to be lowered. A liquid quantity sensor 28 senses the distance the sensor probe 30 is lowered and transmits the information thus sensed to a flocculant adder compressor 81. Thus, the required amount of flocculant to be added is determined.

Then, a flocculant supply tube 33 is connected to an inlet port 22, and a second elbow 27 is connected to a discharge port 82 of a discharging device 6. Once such operations are completed, a start pushbutton is pressed.

Pressing the start pushbutton causes the flocculant adder compressor 81 to force air into a flocculant tank 31 thereby depressing the surface of the flocculant stored therein. Thus, the flocculant is supplied into the waste liquid container 2 through the flocculant supply tube 33 in an amount corresponding to the amount of air forced into the flocculant tank 31. Where there are a plurality of holders 11, appropriate amounts of flocculant are supplied to respective containers 2 on such holders 11 by switching with a change-over valve 83.

After the addition of the flocculant to the waste liquid 1 the vibrator 12 is activated to agitate the waste liquid in the container 2. After completion of the agitation the waste liquid 1 is allowed to stand for a certain period of time so as to be separated into supernatant liquor 3 and flocculate 4.

After the separation a pressure device 70 is actuated to raise a leg 84, so that the bottom of the waste liquid container 2 is pressed up to cause the supernatant liquor 3 in the waste liquid container 2 to be discharged through the discharge port 82. In this case the supernatant liquor 3 may undesirably flow also toward the flocculant supply tube 33 and, hence, it is preferable to provide a check valve in the inlet port 22.

A discharge tube 85 in communication with the discharge port 82 is connected to a hemolysis causing device 47 and is adapted to discharge waste liquid 1 by utilizing the pressure of tap water. Accordingly, when the pressure device 70 is actuated, a washing valve 50 is opened to allow tap water to flow in the discharge tube 85 together with the supernatant liquor 3. Since tap water may undesirably flow into the waste liquid container 2 through the discharge port 82 in this case, it is preferable to provide a check valve in the discharge port 82.

The mixture of the supernatant liquor 3 and tap water flows through the discharge tube 85 and is then sterilized by heating with a sterilizing device 14, followed by being drained.

Subsequent to completion of the drainage, the second elbow 27 and the flocculant supply tube 33 are detached from the discharge port 82 and the inlet port 22, respectively, and then the second elbow 27 is fitted over the inlet port 22. In turn, the deflated waste liquid container 2 is removed from the holder 11 and subjected to its disposal.

We claim:

1. A method of treating a waste liquid containing body fluids including protein components and water content, comprising the steps of: collecting the waste liquid into a deformable container; separating the waste liquid into a supernatant liquor including said water content and a flocculate including said protein components within the container and at room temperature, wherein the step of separating the waste liquid includes adding a polymer flocculant to the waste liquid and then agitating the waste liquid; discharging the supernatant liquor from the container; and disposing of the flocculate remaining in the container together with the container, wherein the step of disposing of the flocculate together with the container includes incinerating the flocculate together with the deformable container.

2. The method as set forth in claim 1, wherein the step of discharging the supernatant liquor includes a treatment for sterilizing the supernatant liquor.

3. The method as set forth in claim 1, wherein the step of disposing of the flocculate together with the container includes causing the container to shrink.

4. The method as set forth in claim 1, wherein in adding the flocculant to the waste liquid a protein solution and an alkaline solution are added to the waste liquid.

5. An apparatus for treating a waste liquid containing body fluids including protein components and water content, comprising a combustible container for collecting the waste liquid therein, a separating device for separating the waste liquid into a supernatant liquor including said water content and a flocculate including said protein components within the container and at room temperature, wherein the separating device includes a polymer flocculant adding device for adding a polymer flocculant to the waste liquid, and an agitating device for agitating the waste liquid added with the flocculant, and a discharging device for discharging the supernatant liquor from the container, wherein the container is portable and deformable by said discharge device.

6. The apparatus as set forth in claim 5, wherein the discharging device is adapted to cause the container to shrink so as to discharge the supernatant liquor from the container.

7. The apparatus as set forth in claim 5, wherein the discharging device includes a suction device for sucking the supernatant liquor from the container.

8. The apparatus as set forth in claim 5, wherein the discharging device includes a pressure device for forcing the supernatant liquor out of the container.

9. The apparatus as set forth in claim 5, wherein the discharging device includes a sterilizing device for sterilizing the supernatant liquor.

10. The apparatus as set forth in claim 9, wherein the sterilizing device includes a heating device for heating the supernatant liquor.

11. The apparatus as set forth in claim 9, wherein the sterilizing device includes a hemolysis causing device for causing hemolysis of red blood cells contained in the supernatant liquor.

* * * * *

UNITED STATES PATENT AND TRADEMARK OFFICE
CERTIFICATE OF CORRECTION

PATENT NO. : 5,945,004
DATED : August 31, 1999
INVENTOR(S) : Junichi OHIRA, et al.

It is certified that error appears in the above-identified patent and that said Letters Patent is hereby corrected as shown below:

On the title page, item [87] the PCT Publication Date should be:

--PCT Pub. Date: Aug. 7, 1997--

Signed and Sealed this

Twenty-third Day of May, 2000

Attest:

Q. TODD DICKINSON

*Attesting Officer*     *Director of Patents and Trademarks*